US008228497B2

(12) United States Patent
Mangan et al.

(10) Patent No.: US 8,228,497 B2
(45) Date of Patent: Jul. 24, 2012

(54) METHOD AND SYSTEM FOR EVALUATING AN OBJECT THAT HAS A REPETITIVE PATTERN

(75) Inventors: Shmuel Mangan, Rehovot (IL); Amir Moshe Sagiv, Beit-Zayit (IL)

(73) Assignee: Applied Materials Israel, Ltd., Rehovot (IL)

( * ) Notice: Subject to any disclaimer, the term of this patent is extended or adjusted under 35 U.S.C. 154(b) by 764 days.

(21) Appl. No.: 12/171,552

(22) Filed: Jul. 11, 2008

(65) Prior Publication Data

US 2009/0066942 A1   Mar. 12, 2009

Related U.S. Application Data

(60) Provisional application No. 60/949,461, filed on Jul. 12, 2007.

(51) Int. Cl.
*G01N 21/00* (2006.01)
(52) U.S. Cl. .................................. 356/237.5
(58) Field of Classification Search ........................ None
See application file for complete search history.

(56) References Cited

U.S. PATENT DOCUMENTS

| | | | | |
|---|---|---|---|---|
| 4,352,564 A * | 10/1982 | Roach | ............................. | 356/521 |
| 4,360,269 A * | 11/1982 | Iwamoto et al. | ............... | 356/426 |
| 4,395,122 A * | 7/1983 | Southgate et al. | ......... | 356/237.5 |
| 5,546,181 A * | 8/1996 | Kobayashi et al. | ......... | 356/237.5 |
| 5,774,222 A * | 6/1998 | Maeda et al. | ................. | 356/394 |
| 5,838,433 A * | 11/1998 | Hagiwara | ..................... | 356/364 |
| 6,137,570 A * | 10/2000 | Chuang et al. | ............. | 356/237.5 |
| 6,556,290 B2 * | 4/2003 | Maeda et al. | ............... | 356/237.2 |
| 6,657,714 B2 * | 12/2003 | Almogy et al. | ............. | 356/237.3 |
| 6,690,469 B1 * | 2/2004 | Shibata et al. | ................ | 356/369 |
| 7,315,364 B2 * | 1/2008 | Baer et al. | ................... | 356/237.2 |
| 7,345,754 B1 * | 3/2008 | Zhao et al. | ................... | 356/237.5 |
| 7,557,912 B2 * | 7/2009 | Fukazawa et al. | ......... | 356/237.2 |
| 2007/0195315 A1 * | 8/2007 | Goldberg et al. | ........... | 356/237.2 |
| 2007/0230768 A1 * | 10/2007 | Adler et al. | ................... | 382/144 |
| 2009/0021749 A1 * | 1/2009 | Yeo et al. | ...................... | 356/601 |

* cited by examiner

*Primary Examiner* — Tarifur Chowdhury
*Assistant Examiner* — Gordon Stock, Jr.
(74) *Attorney, Agent, or Firm* — Tarek N. Fahmi

(57) ABSTRACT

A method and system for evaluating an object that has a repetitive pattern. Illumination optics of an optical unit are adapted to scan a spot of radiation over a repetitive pattern that includes multiple regularly repeating structural elements that are optically distinguishable from their background, generating a diffraction pattern that includes multiple diffraction lobes. Collection optics are adapted to focus radiation from the repetitive pattern onto a detector. The focused radiation includes a single diffraction lobe while not including other diffraction lobes. A grey field detector generates detection signals, responsive to the focused collected radiation. The optical unit is adapted to maintain, at a detection surface of the grew field detector, a radiation pattern that includes a first radiation pattern component resulting from the repetitive pattern and a second radiation pattern component resulting from a defect; wherein the first radiation pattern component is stronger than the second radiation component.

9 Claims, 8 Drawing Sheets

METHOD AND SYSTEM FOR EVALUATING AN OBJECT THAT HAS A REPETITIVE PATTERN

RELATED APPLICATIONS

This application is a NONPROVISIONAL of, claims priority to and incorporates by reference U.S. Provisional Patent Application No. 60/949,461, filed Jul. 12, 2007.

FIELD OF THE INVENTION

This invention is generally in the field of automatic optical evaluation of objects such as masks or wafers that include a repetitive pattern.

BACKGROUND OF THE INVENTION

Objects such as wafers and photomasks are evaluated by illuminating the object by radiation and detecting signals that are scattered from the object, are reflected from the object or pass through the object. The radiation can include light radiation, ultra violet radiation and deep ultra violet radiation.

The detected signals are processed by one of few well known defect detection algorithms. Some of the algorithms include comparing detection signals that represent an inspected pattern to corresponding signals that represent a reference pattern. The latter may be for example a corresponding similar pattern in another region of the object under inspection (commonly known as "Die-to-Die" inspection). Another example is a synthetic pattern produced by an appropriate physical modeling of a desired design (as in "Die-to-Database" comparison).

In many cases the inspected object includes a repetitive pattern. The repetitive pattern includes multiple regularly repeating structural elements and their background. These multiple regularly repeating structural elements are optically distinguishable from their background. For example, while the multiple regularly repeating structural elements can be opaque the background can be transparent.

With either method, detection signals of the object (that may form an image of the inspected object), are subtracted from reference signals (that may form an image of a reference object), and some simple metric of the difference, such as its peak absolute value, is used for determining whether a defect exists.

The intensities of the detection signals of the inspected pattern can be proportional to the squared absolute (complex) amplitude of the electric fields associated with the inspected object but can, additionally or alternatively, be proportional to the field perturbation due to the presence of the defect.

Defect information representative of defects that appear over regions of the pattern that give rise to low-amplitude image electric field may typically be substantially weaker (and even unnoticeable) in relation to defects that appear over regions of the pattern where the resulting image electric field has a substantial amplitude.

FIG. 1 illustrates a non-limiting example of portion 12 of a repetitive pattern 11 of an object 10. Repetitive pattern 11 includes multiple substantially opaque regularly repeating structural elements such as lines 14(1), 14(2) and 14(3) that are formed over a background such as transparent line 15. A substantially transparent defect 16 is located above (or within) line 14(3) while another substantially opaque defect 17 is located above (or within) background 15. It is expected that defect information relating to defect 16 will hardly be noticeable, or will not be as noticeable as defect 17 that is located at a position in which the value (amplitude, field strength) of the pattern information is high. It is noted that in general, similar defects that are located within different backgrounds can result in different detection signals.

FIG. 2 illustrates prior art detection signals obtained from scanning that portion of the repetitive pattern.

Oscillating curve 24 illustrates the electromagnetic field expected to be formed on a sensor as a result of an ideally defect free reference repetitive pattern. The net electromagnetic field received (at a sensor) at the location of defect 16 is denoted 26 and the electromagnetic field received at the position of defect 17 is denoted 27. On the bottom panel of FIG. 2, the net intensities received at a sensor of defects 16 and 17 are illustrated, denoted 26' and 27', respectively.

As can be clearly seen in FIG. 2, the difference in electric field due to defect 16 is much smaller than that due to defect 17. As a result, defect information relating to defect 16 can be hardly noticeable by an inspection process. Hence there is a need for systems and methods that enable defect detection also at positions where the amplitude of the pattern field is small.

SUMMARY OF THE INVENTION

A system for evaluating an object having a repetitive pattern, the system includes an optical unit; wherein the optical unit includes illumination optics, collection optics and a radiation detector; wherein the illumination optics is adapted to scan a spot of radiation over the repetitive pattern such as to generate a diffraction pattern that includes multiple diffraction lobes; wherein the collection optics is adapted to focus onto a detector radiation from the repetitive pattern; wherein the focused radiation includes a single diffraction lobe while not including other diffraction lobes; wherein the detector generates detection signals, responsive to the focused collected radiation; wherein the optical unit is adapted to maintain, at a detection surface of the detector, a radiation pattern that comprises a first radiation pattern component that results from the repetitive pattern and a second radiation pattern component that results from the defect; wherein the first radiation pattern component is stronger than the second radiation component. The repetitive pattern includes multiple regularly repeating structural elements that are optically distinguishable from their background.

Conveniently, the first radiation pattern component is substantially constant.

Conveniently, the collection optics is adapted to collect radiation that includes multiple diffraction lobes, to block all diffraction lobes except a single diffraction lobe; and to focus onto the detector radiation from the repetitive pattern that includes that single diffraction lobe.

Conveniently, the collection optics is adapted to focus onto the detector radiation from the repetitive pattern; wherein the focused radiation includes a single diffraction lobe and a portion of another diffraction lobe.

Conveniently, the collection optics is adapted to collect radiation that includes multiple diffraction lobes and to block all diffraction lobes except the single diffraction lobe and the portion of another diffraction lobe.

Conveniently, the collection optics is adapted to collect radiation that includes a single diffraction lobe while not collecting other diffraction lobes.

Conveniently, the collection optics is adapted to collect radiation that includes a single diffraction lobe and at least a portion of another diffraction lobe while not collecting further diffraction lobes.

Conveniently, at least one entity out of the multiple regularly repeating structural elements and their background are at least partially transparent and wherein at least one lens of the collection optics and at least one lens of the illumination optics are positioned at opposite sides of the object.

Conveniently, the multiple regularly repeating structural elements and their background are at least partially reflective and wherein at least one lens of the collection optics and at least one lens of the illumination optics are positioned at a same side of the object.

Conveniently, the system includes a processing unit that is adapted to process the detection signals in order to evaluate the object.

A method for evaluating an object having a repetitive pattern, the method includes: (i) scanning a spot of radiation over the repetitive pattern such as to generate a diffraction pattern that includes multiple diffraction lobes; wherein the repetitive pattern includes multiple regularly repeating structural elements that are optically distinguishable from their background; (ii) collecting radiation from the repetitive pattern and focusing onto a detector focused radiation that includes a single diffraction lobe while not including other diffraction lobes; wherein at a detection surface of the detector, the focused radiation has a radiation pattern that comprises a first radiation pattern component that results from the repetitive pattern and a second radiation pattern component that results from the defect; wherein the first radiation pattern component is stronger than the second radiation component; and (iii) detecting the focused collected radiation and in response generating detection signals, by a detector.

Conveniently, the first radiation pattern component is substantially constant.

Conveniently, the method includes collecting radiation that includes multiple diffraction lobes and blocking all diffraction lobes except a single diffraction lobe.

Conveniently, the collecting includes focusing onto the detector radiation that includes a single diffraction lobe and a portion of another diffraction lobe.

Conveniently, the method includes collecting radiation that includes multiple diffraction lobes and blocking all diffraction lobes except a single diffraction lobe and a portion of another diffraction lobe.

Conveniently, the method includes collecting radiation that includes a single diffraction lobe while not collecting other diffraction lobes.

Conveniently, the method includes collecting radiation that includes a single diffraction lobe and at least a portion of another diffraction lobe while not collecting further diffraction lobes.

Conveniently, the multiple regularly repeating structural elements and their background are at least partially transparent and wherein the method includes collecting radiation that passes through the object.

Conveniently, at least one entity out of the multiple regularly repeating structural elements and their background is at least partially reflective and wherein the method includes collecting radiation that is reflected from the object.

Conveniently, the method includes processing the detection signals in order to evaluate the object.

BRIEF DESCRIPTION OF THE DRAWINGS

In order to understand the invention and to see how it may be carried out in practice, an embodiment will now be described, by way of non-limiting example only, with reference to the accompanying drawings, in which.

DETAILED DESCRIPTION

Figure 1:
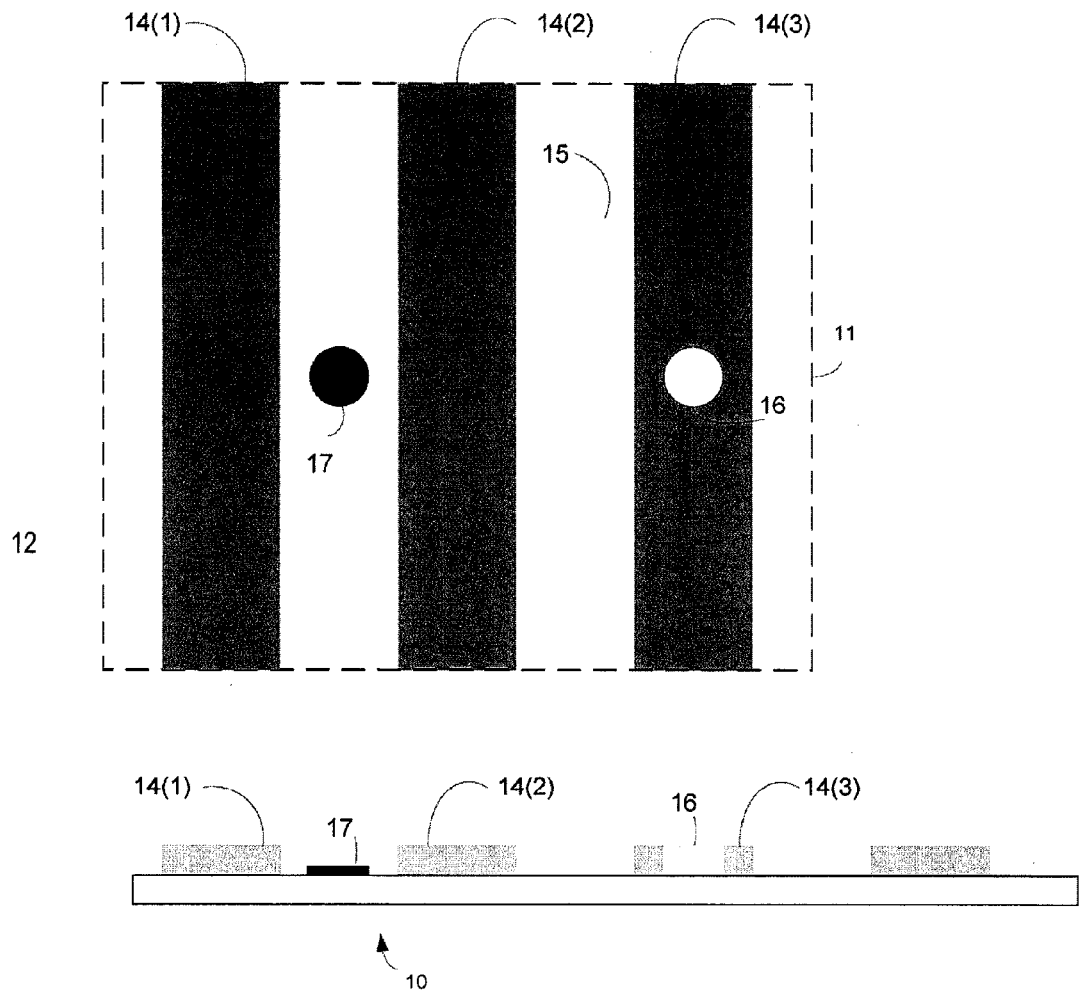
FIG. 1 illustrates a portion of repetitive pattern and two defects.
Figure 2:
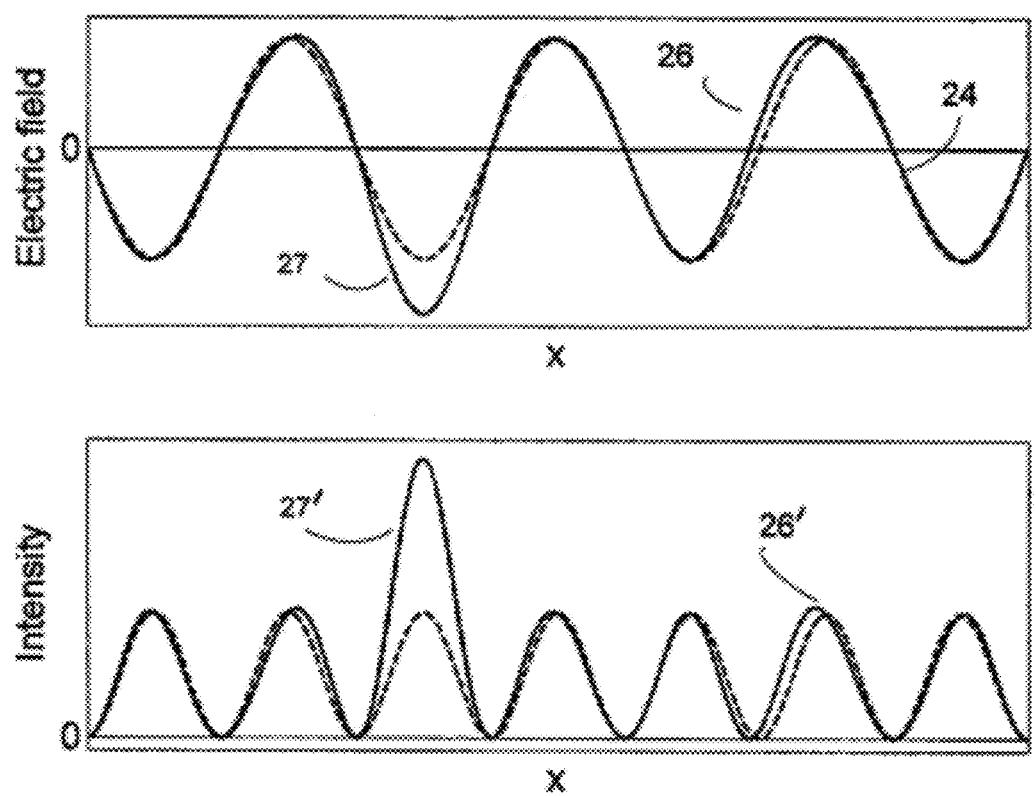
FIG. 2 illustrates prior art detection signals obtained from scanning that portion of the repetitive pattern.

A method and a system for evaluating an object that includes a repetitive pattern are provided. It is noted that the system (or method) can apply transmissive inspection schemes, reflective inspections schemes, can use a pulsed light source or a continuous light source, can utilize visible light, utilize ultraviolet light or utilize deep ultraviolet light, can utilize on-axis illumination, off-axis illumination, can include multiple detectors, can include one or more spatial filters or apertures, can perform defect detection, defect review, metrology, and the like.

For simplicity of explanation the following figures refer to an inspection of a mask by applying a transmissive inspection scheme. It is noted that other objects (such as but not limited to wafers) can be inspected. It is noted that even a mask can be inspected in a reflective mode.

Those of skill in the art sill appreciate that the intensity of a detection signal is proportional to the squared absolute (complex) amplitude of an electric field formed on a detector. Accordingly, when a detection signal is compared to a reference signal, the difference ($\delta I$) between these signals can be responsive to the sum of: (i) a square ($|\delta E|^2$) of the perturbation of the electromagnetic field introduced by a defect, and (ii) a product of the perturbation of the electromagnetic field ($\delta E$) introduced by the defect, the electromagnetic field introduced by a defect-free pattern ($E_{ref}$) and the cosine (cos $\phi$) of the phase angle between these electromagnetic fields.

In mathematical terms, the difference ($\delta I$) between the reference intensity ($I_{ref}$) and the intensity of the inspected pattern (I) can be described as:

$$\delta I = I - I_{ref}$$
$$= |E + E_{ref}|^2 - |E_{ref}|^2$$
$$= (|E_{ref}|^2 + 2|E_{ref} \delta E|\cos\phi + |\delta E|^2) - |E_{ref}|^2 =$$
$$= 2|E_{ref} \delta E|\cos\phi + |\delta E|^2.$$

Assuming that a repetitive pattern is evaluated, $E_{ref}(x)$ is the electromagnetic field expected from an ideally defect-free reference repetitive pattern (also referred to as pattern information), $\delta E(x)$ is a perturbation to the electromagnetic field introduced by the presence of the defect (also referred to as defect information), and $\phi$ is a phase between these two fields.

In regions of the image of the mask where the electromagnetic field introduced by the pattern is weak in comparison to the perturbation δE, (i.e., where $|E_{ref}(x)|<<|\delta E(x)|$), the defect signal δI is dominated by the term quadratic in δE, viz. $\delta I \propto |\delta E|^2$. This can occur, for example, when a transparent defect is located within an opaque regularly repeating structural element.

Conversely, in regions where the electromagnetic field introduced by, the pattern is strong in comparison to the perturbation δE, viz. $|E_{ref}(x)|>>|\delta E(x)|$, δI is dominated by the cross-term $2|E_{ref}\delta E|\cos \phi$, and thus scales linearly with δE. This can occur, for example, when an opaque defect is located within a transparent regularly repeating structural element.

When these two regimes are compared, it is noticed that the second case is much more favorable for defect detection, since it has the potential to amplify weak defect information that otherwise would be too weak to be captured by the detection system.

Accordingly, the suggested methods and systems give rise to an electromagnetic field introduced by the pattern that does not diminish to small amplitude values below an electromagnetic field introduced by the presence of the defects, that is the suggested methods and systems avoid the situation where $|E_{ref}(x)|<<|\delta E(x)|$. This relationship is maintained at the detector.

Conveniently, the system and method provide, at a detection surface of the detector, a radiation pattern that includes a first radiation pattern component that results from the repetitive pattern and a second radiation pattern component that results from the defect. The first radiation pattern component is stronger than the second radiation component.

The above mentioned detector differs from a "classic" dark field detector as it detects some pattern information. The above mentioned detector includes a surface that interacts with the radiation. This surface can be referred to as a sensing surface or a detection surface.

Figure 3:
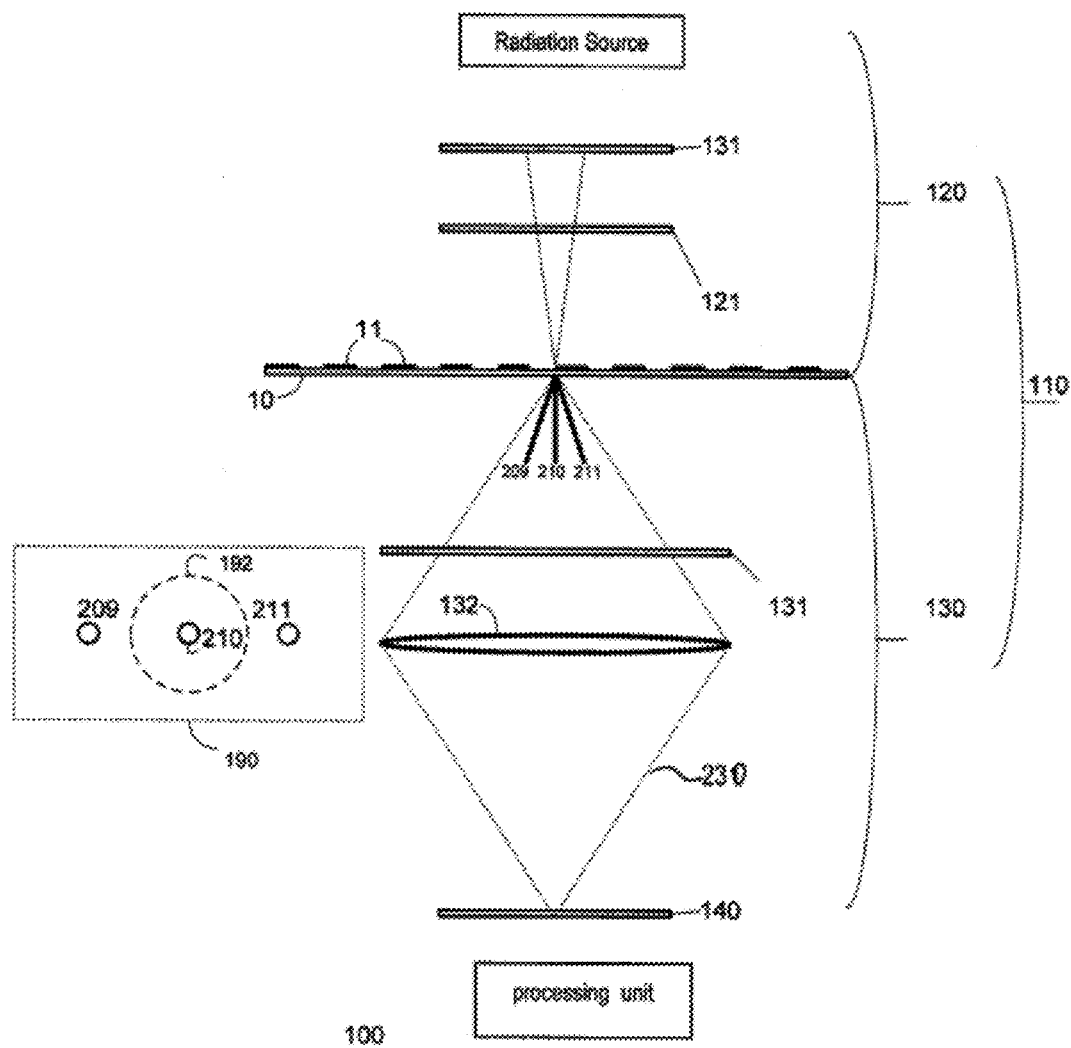
FIG. 3 illustrates a system for evaluating an object having a repetitive pattern and a pupil aperture according to an embodiment of the invention.

FIG. 3 illustrates system 100 according to an embodiment of the invention.

System 100 includes optical unit 110. Optical unit 10 is adapted to optically attenuate repetitive pattern information in relation to defect information. Optical unit 110 suppresses the modulation of the radiation pattern at the detector and at the same time achieves a strong enhancement of the defect information.

Optical unit 110 includes illumination optics 120, collection optics 130 and detector 140. It is noted that system 100 can include additional detectors.

Illumination optics 120 is adapted to scan a spot of radiation over repetitive pattern 11 of mask 10 such as to generate a diffraction pattern that includes multiple diffraction lobes. For simplicity of explanation FIG. 3 illustrates the zero order diffraction lobe 210, and two additional diffraction lobes 209 (minus one order diffraction lobe) and 211 (first order diffraction lobe).

Illumination optics 120 or system 100 can include a radiation source (not shown) that can be a quasi-monochromatic source, such as an ArF Eximer 193 nm laser.

Conveniently, illumination optics 120 includes spatial filter 121 that includes an aperture (also referred to as pupil plane aperture) through which radiation propagates before reaching mask 10.

Spatial filter 121 can cause the numerical aperture of illumination optics 120 to differ from the numerical aperture of collection optics 130. Sigma is the ratio between the illumination optics numerical aperture and the collection optics numerical aperture. Spatial filter 121 can affect sigma to have a desired value. Sigma can be medium, can be small, very small, large and even very large.

Collection optics 130 is adapted to focus onto detector 140 radiation (also referred to as focused radiation) 230 from repetitive pattern 11. Focused radiation 230 includes a single diffraction lobe (such as zero order diffraction lobe 210) while not including other diffraction lobes.

Collection optics 130 includes spatial filter 131 and objective lens 132. It may also include additional lenses (or other optical components) which are not shown for simplicity of explanation. These additional lenses can be used for relaying an acquired image, image magnification or image demagnification, but this is not necessarily so.

It is noted that although FIG. 3 illustrates that zero order diffraction lobe 210 is directed towards detector 140, other diffraction lobes can be focused onto detector 140, for example by performing off-axis collection. It is also noted that multiple detectors can be positioned so as to receive diffraction lobes of different orders.

Detector 140 generates detection signals, responsive to focused radiation 230. The detector can be a Charged Coupled Device (CCD) array but this is not necessarily so. Other image detectors can be used.

According to an embodiment of the invention the numerical aperture of collection optics 130 is large enough to collect multiple diffraction lobes. In order to allow only a single diffraction lobe to be focused onto detector 140, spatial filter 131 blocks all diffraction orders (or all diffraction orders but one) originating from pattern 11. Spatial filter 131 can precede objective lens 132 or follow objective lens 132. For simplicity of explanation spatial filter 131 is illustrated as preceding objective lens 132. Spatial filter 131 can be located in a back focal plane of objective lens 132. Objective lens 132 can include multiple lenses and in this case spatial filter 131 can even be located between the multiple lenses.

It is noted that on-axis illumination can be used for binary masks and attenuated phase shift masks while alternating phase shift masks may require off-axis illumination.

It is noted that one type of illumination (on-axis or off-axis) can also be used when illuminating pure phase shifting masks, where there are no attenuating materials whatsoever.

A radiation pattern 190 illustrates that without spatial filter 131 the objective lens 132 would have focused three diffraction lobes 209, 210 and 211 towards detector 140 but due to spatial filter 131 diffraction lobes 209 and 211 are blocked while the zero order diffraction lobe 210 passes though an aperture of spatial filter 131. The effect of spatial filter 131 is illustrated by circle 192 that surrounds diffraction lobes 210 while not surrounding the other diffraction lobes 209 and 211.

Since for the image field to posses any modulation, at least two distinct mutually coherent beams must be projected on detector 140, system 100 ensures that the image field is not modulated, but rather it becomes a non-vanishing constant, with an amplitude that is determined by the transmission, phase and filling factor of the structural elements in the repetitive pattern of mask 10.

If, for example, mask 10 is an attenuated phase shift mask, then system 100 can illuminate this mask and generate an image field whose amplitude is a factor $f_{fill}\lfloor 1+T^{1/2} \cos \phi_{PSM} \rfloor$ times the amplitude due to a large transparent region on the mask. Here $f_{fill}$ is the fraction of the pattern area with transmission $T \neq 1$, and $\phi_{PSM}$ is the phase shift associated with it. For a 50% duty-cycle lines-and-spaces pattern on a 6% transmission MoSi phase shift mask, this factor equals 0.377. This results in a pattern information portion of the detection signals that is substantially constant and is higher than the amplitude of defect information, thus contributing to a strong defect signal that may easily be detected.

Figure 4:
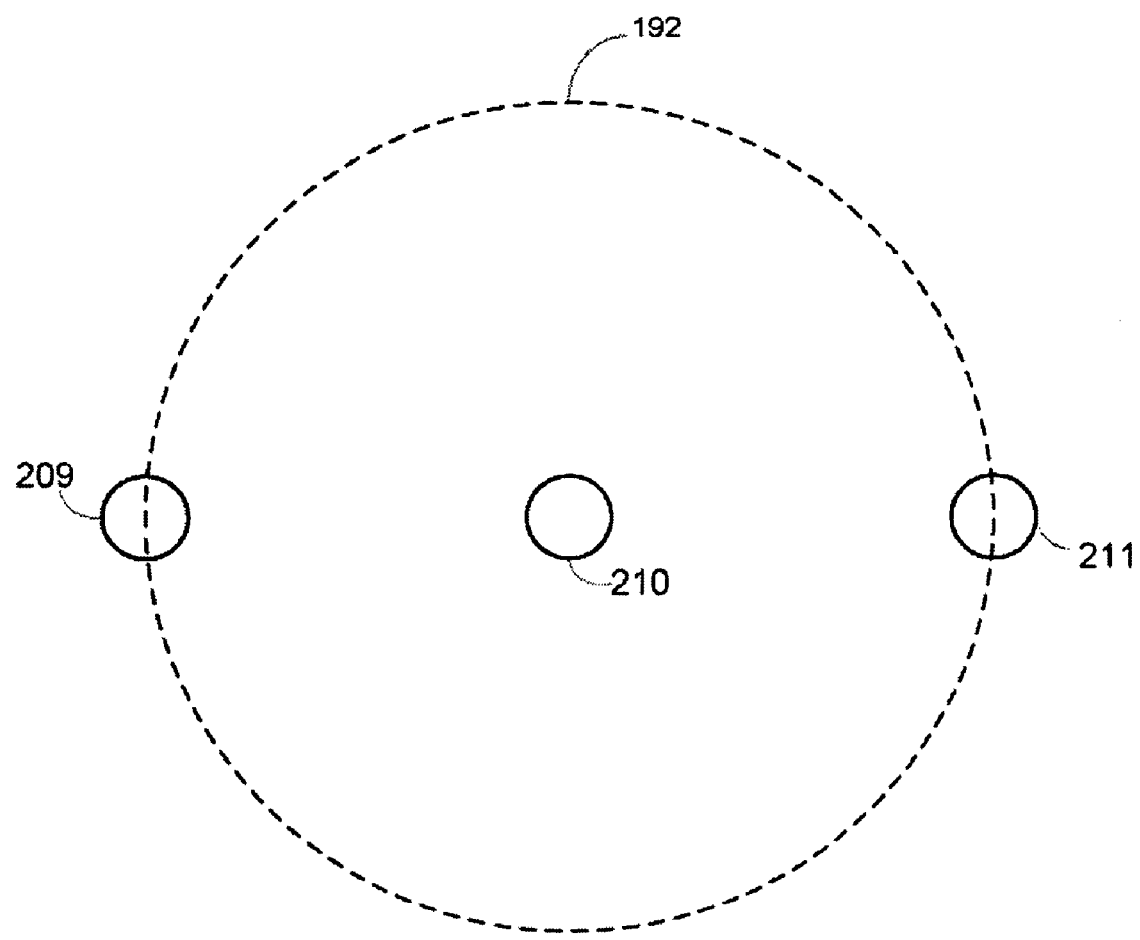
FIG. 4 illustrates a radiation pattern across an objective lens according to another embodiment of the invention.

According to another embodiment of the invention, spatial filter 131 passes zero order diffraction lobe 210 and a portion of at least one other diffraction lobe out of diffraction lobes 209 and 211. Conveniently, a portion of diffraction lobe 209 and a portion of diffraction lobe 211 pass through spatial filter 131. Such a filtering scheme is illustrated in FIG. 4.

Figure 5:
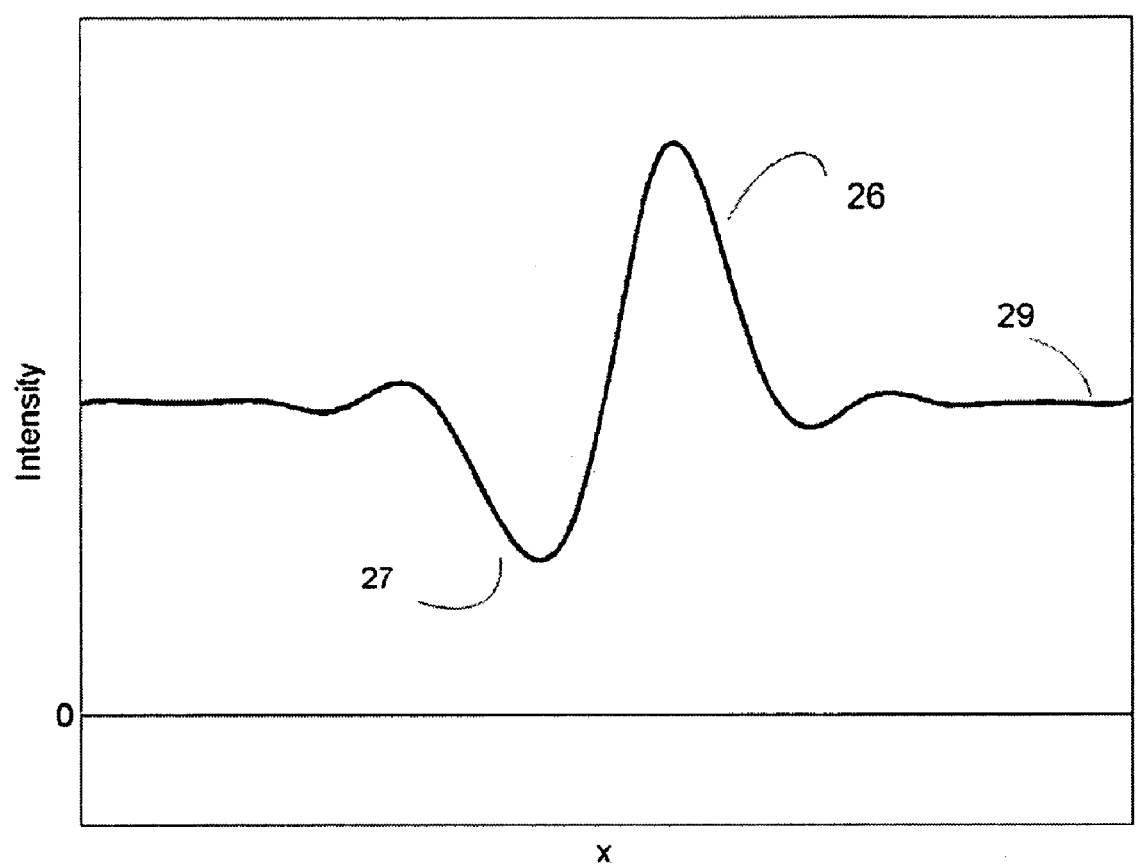
FIG. 5 illustrates detection signals obtained from scanning a portion of the repetitive pattern of the pattern by the system of FIG. 3, according to an embodiment of the invention.

FIG. 5 illustrates a radiation pattern obtained at the detection surface of detector 140, according to an embodiment of the invention. The radiation pattern includes first radiation pattern component 29 that results from the repetitive pattern. This first radiation pattern component is flat—it does not change across the image of the repetitive pattern. A second radiation pattern component (26 and 27) that results from defects 16 and 17 is weaker than first radiation pattern component 29. It is superimposed on the first radiation pattern component 29.

Figure 6:
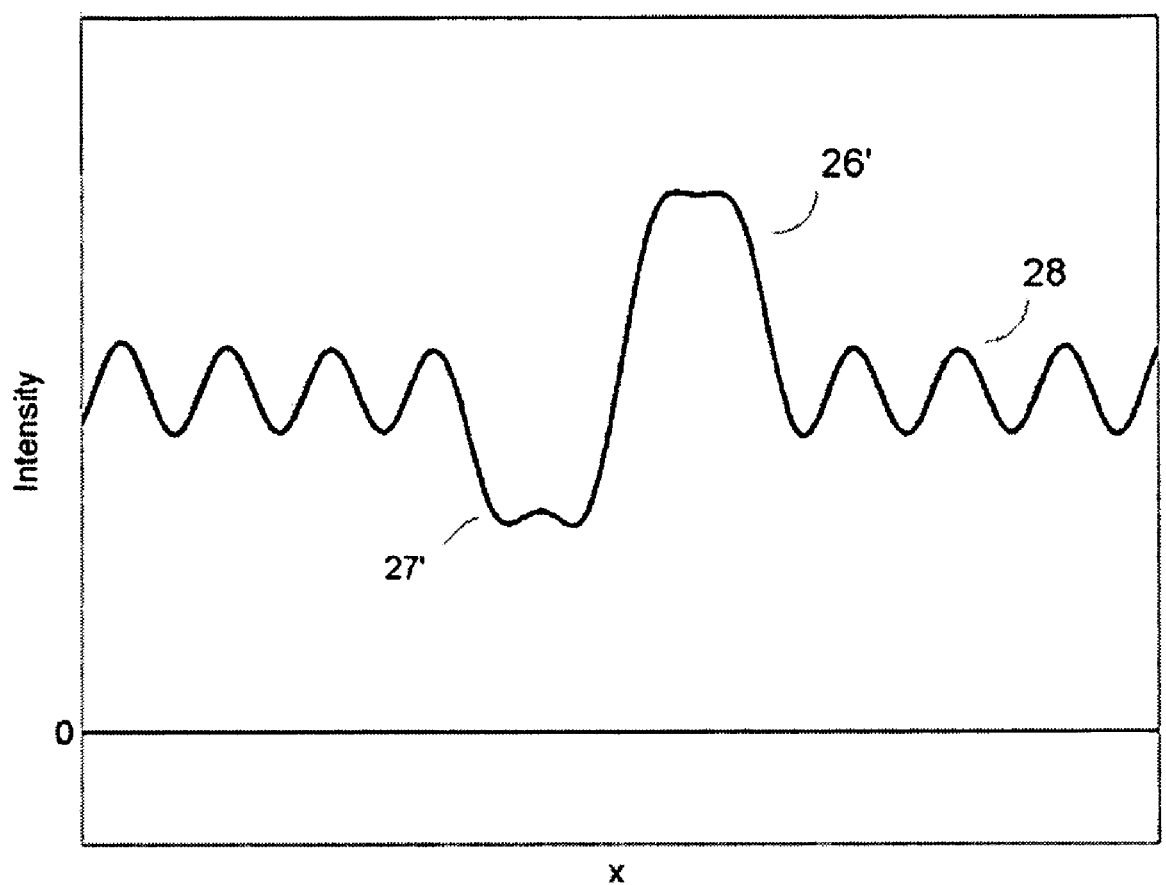
FIG. 6 illustrates detection signals obtained from scanning a portion of the repetitive pattern by the system of FIG. 3, according to another embodiment of the invention.
Figure 7:
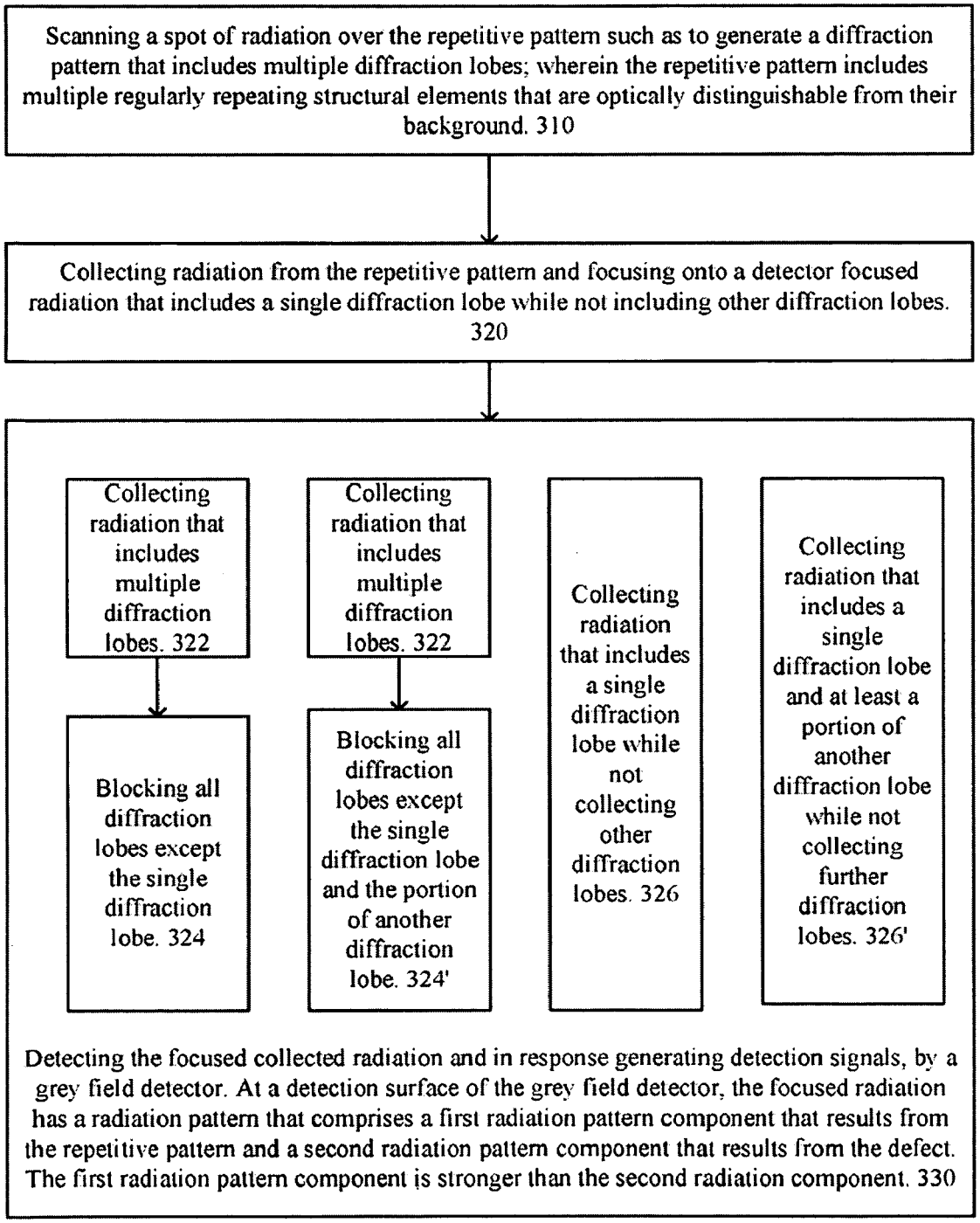
FIG. 7 illustrates a method for evaluating a object having a repetitive pattern according to an embodiment of the invention.

FIG. 6 illustrates a radiation pattern obtained at the detection surface of detector 140, according to another embodiment of the invention. The radiation pattern includes first radiation pattern component 28 that results from the repetitive pattern. This first radiation pattern component 28 is not flat—is includes a weakly oscillating component that changes in a weakly oscillating manner across the repetitive pattern. A second radiation pattern component (26' and 27') that results from defects 16 and 17 is weaker than first radiation pattern component 28. The second radiation pattern is superimposed on first radiation pattern component 28. The weak oscillation can be a sinusoidal FIG. 7 illustrates method 300 for evaluating a pattern of a mask or a wafer according to an embodiment of the invention.

Method 300 can be executed by system 100 but this is not necessarily so.

Method 300 starts by stage 310 of scanning a spot of radiation over the repetitive pattern such as to generate a diffraction pattern that includes multiple diffraction lobes; wherein the repetitive pattern includes multiple regularly repeating structural elements that are optically distinguishable from their background.

Stage 310 is followed by stage 320 of collecting radiation from the repetitive pattern and focusing onto a detector focused radiation that includes a single diffraction lobe while not including other diffraction lobes.

Stage 320 is followed by stage 330 of detecting the focused collected radiation and in response generating detection signals, by a detector. At a detection surface of the detector, the focused radiation has a radiation pattern that comprises a first radiation pattern component that results from the repetitive pattern and a second radiation pattern component that results from the defect. The first radiation pattern component is stronger than the second radiation component.

Conveniently, the first radiation pattern component is substantially constant.

Conveniently, stage 320 includes stage 322 of collecting radiation that includes multiple diffraction lobes and stage 324 of blocking all diffraction lobes except the single diffraction lobe.

Conveniently, stage 320 includes focusing onto the detector radiation that includes a single diffraction lobe and a portion of another diffraction lobe.

Conveniently, stage 320 includes stage 322 of collecting radiation that includes multiple diffraction lobes and stage 234' of blocking all diffraction lobes except the single diffraction lobe and the portion of another diffraction lobe.

Conveniently, stage 320 includes stage 326 of collecting radiation that includes a single diffraction lobe while not collecting other diffraction lobes.

Conveniently, stage 320 includes stage 326' of collecting radiation that includes a single diffraction lobe and at least a portion of another diffraction lobe while not collecting further diffraction lobes.

Figure 8:
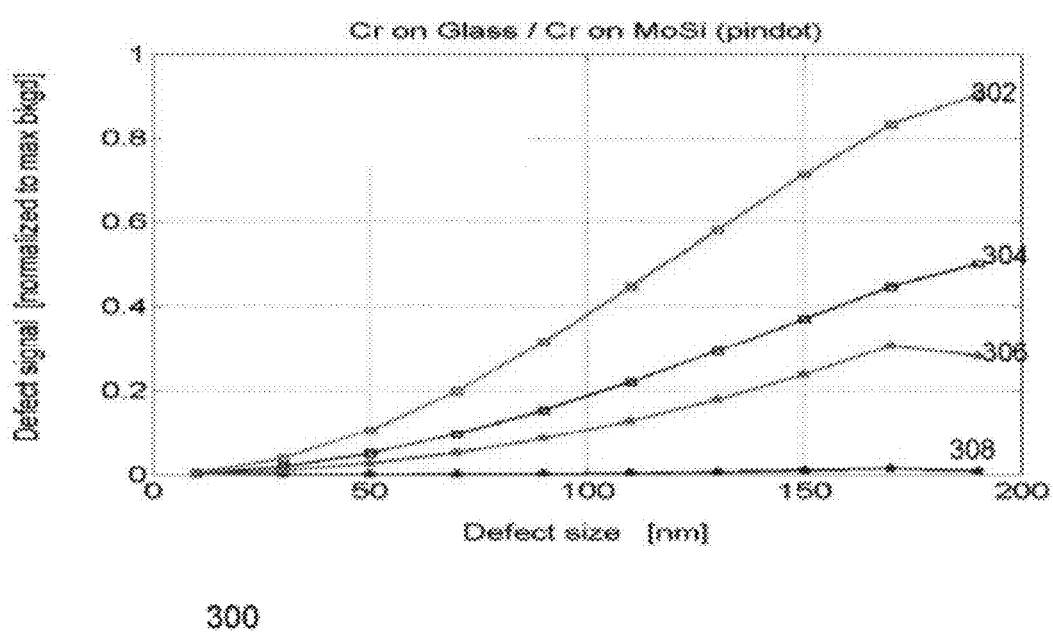
FIG. 8 illustrates sample preliminary results obtained from simulating a mask inspection stem.

FIG. 8 illustrates sample results 300 obtained from a simulation of a mask inspection system according to an embodiment of the invention.

FIG. 8 illustrates the relationship between defect size (x-axis) and a normalized amplitude of a defect signal (y-axis). The defect is a small square of Chromium (opaque defect) either on a 6% MoSi lines (opaque pattern) or on a glass background in a periodic lines-and-spaces periodical pattern of an attenuated phase shifting mask. Two half-pitches (of the repetitive pattern) are considered (65 nm and 45 nm @ 1X, i.e. 260 nm and 180 nm at the plane of the mask), and the Chromium defects sizes range from 10 nm to the scale of the half pitch.

Cure 302 illustrates the relationship between the Chromium defect size (when located on a glass background) and the defect signal, when using grey field detection. Curve 304 illustrates the relationship between the Chromium defect size (when located on a glass background) and defect signal when using bright field (Aerial imaging) detection. Curve 306 illustrates the relationship between the Chromium defect size (when located on a MoSi line) and defect signal when using grey field detection. Curve 308 illustrates the relationship between the Chromium defect size (when located on a MoSi line) and defect signal when using bright field (Aerial imaging) detection.

The defect signal is normalized to the maximum of the background/pattern intensity, to reflect the dramatic increase in dynamic range attainable with grey-field detection, compared to bright-field detection.

With a signal-to-noise (SNR) ratio at the 1% level, defects larger than ~60 nm size can easily be detected. In fact, FIG. 8 shows that by applying the above mentioned methods and systems, the signal of all small defects scales as $[NA \times defect\ size]^2$, irrespective of the particular nature of the defect. Wherein NA is the numerical aperture of the collection path.

Those skilled in the art will readily appreciate that various modifications and changes can be applied to the embodiments of the invention as hereinbefore described without departing from its scope defined in and by the appended claims.

What is claimed is:

1. A system comprising: an optical unit; wherein the optical unit comprises an illumination optics, a collection optics, and a grey field detector;

wherein the illumination optics is adapted to scan a spot of radiation over an object having a repetitive pattern of multiple regularly repeating structural elements such as to generate a diffraction pattern that comprises multiple diffraction lobes;

wherein the collection optics is adapted to collect and filter the diffraction pattern, wherein the filtered diffraction pattern comprises a single diffraction lobe while not comprising other diffraction lobes, wherein the collection optics is adapted to collect and filter the diffraction pattern to produce a filtered diffraction pattern that consists of a single diffraction lobe;

wherein the grey field detector is adapted to collect a focused radiation pattern from the collection optics and generate detection signals, wherein the detection signals include a first pattern component that results from scanning the repetitive pattern and a second pattern component that results from scanning a defect on the object; and wherein the detection signals include oscillating signals of the first pattern component and oscillating signals of the second pattern component, the optical unit being adapted to optically attenuate at least one of the oscillating signals of the first pattern component and the oscillating signals of the second pattern component to weaken the oscillating signals of the first pattern component so as to be distinguishable from the oscillating signals of the second pattern component.

2. The system according to claim 1 wherein the first pattern component is substantially constant.

3. The system according to claim 1 wherein the object includes a background and at least one of a structural element and the background are at least partially transparent and wherein a portion of the collection optics and a portion of the illumination optics are positioned at opposite sides of the object.

4. The system according to claim 1 comprising a processing unit that is adapted to process the detection signals in order to evaluate the object.

5. A method comprising:

scanning, with illumination optics, a spot of radiation over an object having a repetitive pattern of multiple regularly repeating structural elements such as to generate a diffraction pattern that comprises multiple diffraction lobes;

collecting the diffraction pattern with collection optics;

filtering, by the collection optics, the diffraction pattern such that the filtered diffraction pattern consists of a single diffraction lobe;

collecting, by a grey field detector, the filtered diffraction pattern;

generating, by the grey field detector, detection signals based on the filtered diffraction pattern, wherein the detection signals include a first pattern component that results from scanning the repetitive pattern and a second pattern component that results from scanning a defect on the object, the detection signals including oscillating signals of the first pattern component and the second pattern component; and optically attenuating at least one of the oscillating signals of the first pattern component and the oscillating signals of the second pattern component to weaken the oscillating signals of the first pattern component so as to be distinguishable from the oscillating signals of the second pattern component.

6. The method according to claim 5 wherein the first pattern component is substantially constant.

7. The method according to claim 5 comprising collecting radiation that comprises a single diffraction lobe while not collecting radiation that comprises other diffraction lobes.

8. The method according to claim 5 wherein the object includes a background and at least one of a structural element and the background are at least partially transparent, the method further comprising:

collecting radiation that passes through the at least one structural element and background.

9. The method according to claim 5 comprising processing the detection signals in order to evaluate the object.

* * * * *